United States Patent [19]

Petrick

[11] Patent Number: 5,632,777
[45] Date of Patent: May 27, 1997

[54] METHOD OF INFLATING A PROSTHESIS

[76] Inventor: Timothy B. Petrick, 9006 Trinity Gardens North, Brooklyn Park, Minn. 55443

[21] Appl. No.: 452,405

[22] Filed: May 26, 1995

Related U.S. Application Data

[62] Division of Ser. No. 207,023, Mar. 4, 1994, abandoned.
[51] Int. Cl.$^6$ .................................................. A61F 2/04
[52] U.S. Cl. ........................... 623/11; 623/7; 623/8; 623/12
[58] Field of Search .................... 623/7, 8, 11, 12

[56] References Cited

U.S. PATENT DOCUMENTS 3,934,274 1/1976 Hartley, Jr. .................... 623/8
4,253,201 3/1981 Ross et al. .................... 623/8
4,662,357 5/1987 Pierce et al. .................... 623/11

*Primary Examiner*—John G. Weiss
*Assistant Examiner*—Francis K. Cuddihy

[57] ABSTRACT

Testicular prosthesis and method of manufacturing wherein the testicular prosthesis has a saline or other biologically safe fluid filled silicone elastomer shell which includes a self-sealing injection site for filling the prosthesis and a tab for suturing the testicular prosthesis into position in the scrotum. A method of filling and a method of identifying and serialization is also provided.

18 Claims, 7 Drawing Sheets

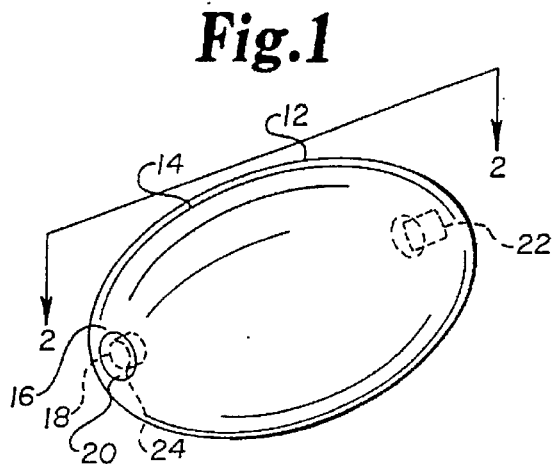
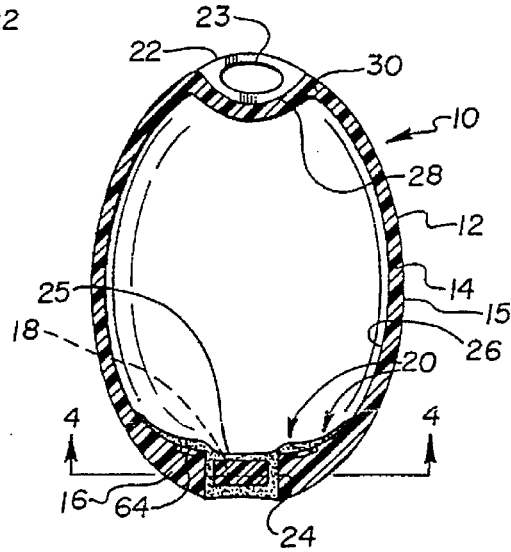
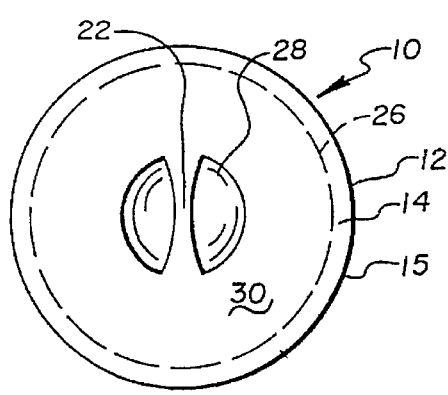
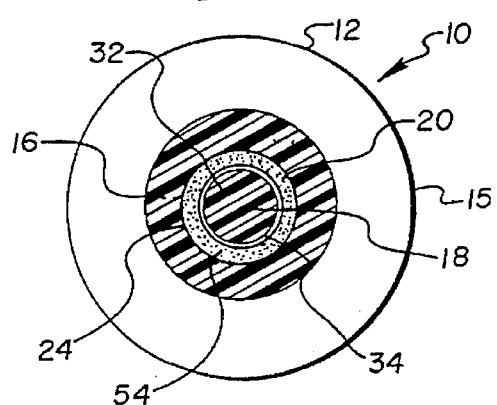
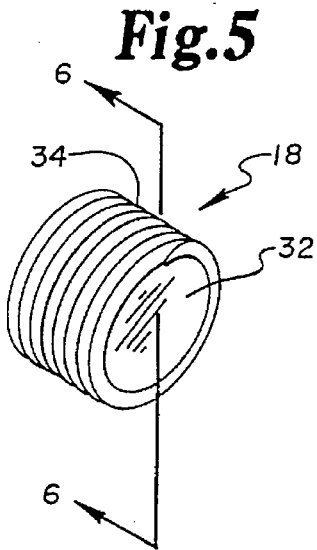

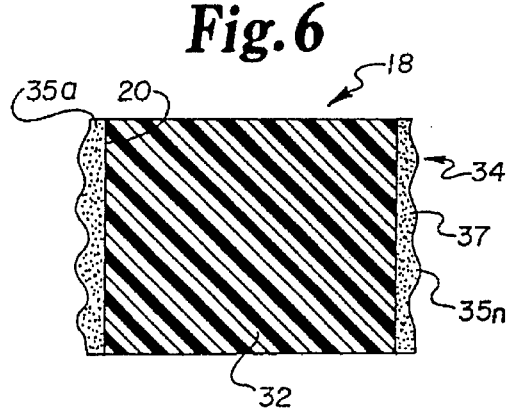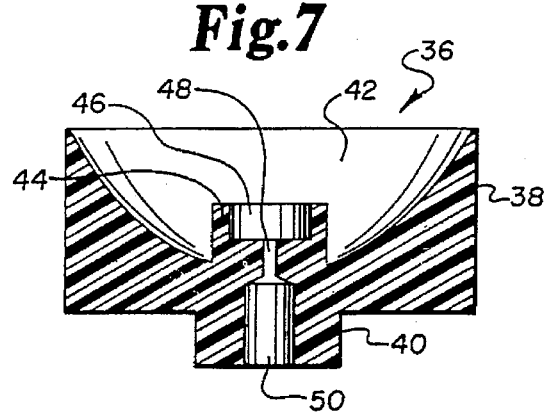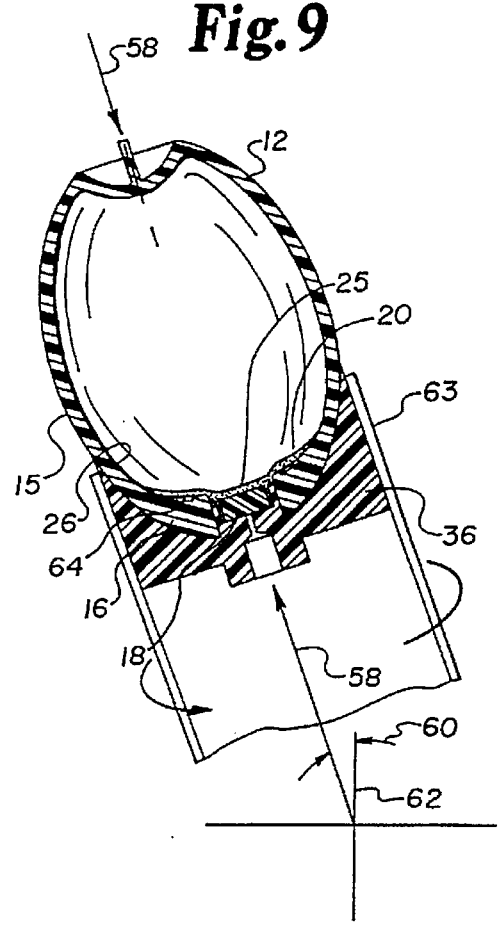

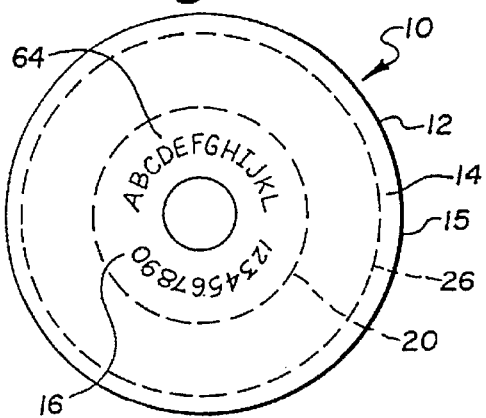
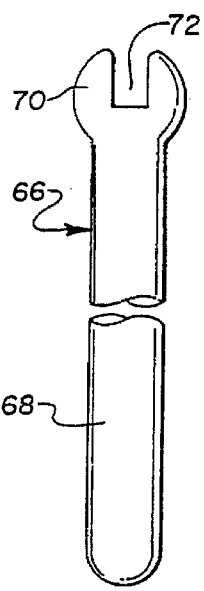
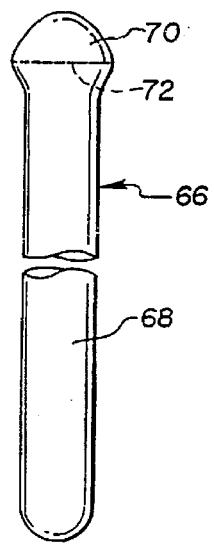
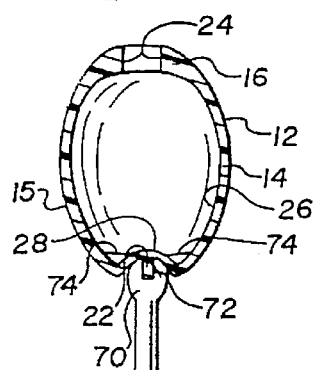
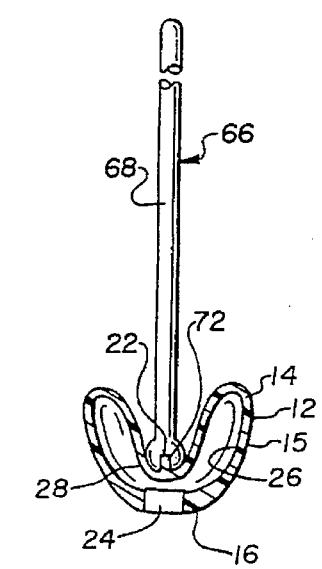
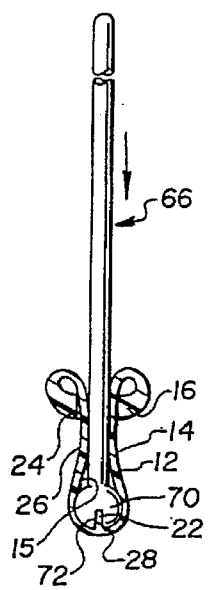
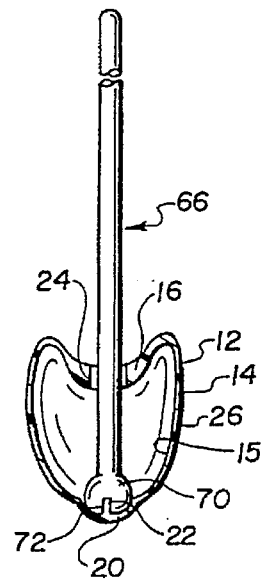

METHOD OF INFLATING A PROSTHESIS

This application is a divisional of application Ser. No. 08/207,023 filed on Mar. 4, 1994 now abandoned, entitled Testicular Prosthesis and Method of Manufacturing and Filling, and the benefit of priority under 35 USC§120 is hereby claimed.

BACKGROUND OF THE INVENTION

The present invention pertains to a prosthesis, and more particularly, relates to a testicular prosthesis having a saline filled elastomer shell which includes a self-sealing injection site through which saline or other biologically safe fluid is injected. A method of manufacturing and filling is also disclosed.

Prior art testicular prosthesis have been of solid material or have been filled with a soft silicone elastomer or a silicone gel. See *"The Why and How of Synthetic Replacement Testicles"* by Joseph Ortenberg, M. D. and Robert G. Kupper, M.D. in *Contemporary Urology*, October 1991, pp 23-32.

The present invention improves on the prior art devices by providing a testicular prosthesis of a silicone elastomer having a self-sealing filling injection site which is incorporated to provide for filling of the testicular prosthesis with a saline solution or other biologically safe fluid.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

SUMMARY OF THE INVENTION

The general purpose of the present invention is to provide a shell member similar in size and shape to that of a testicle. Preferably, a self-sealing injection site the subject of a co-pending application Ser. No. 08/205,995 filed on Mar. 4, 1994, in the name of Timothy B. Petrick, entitled *IMPROVED SELF-SEALING INJECTION SITES AND PLUGS, IMPLANTABLE PROSTHESIS AND OTHER DEVICES UTILIZING SAME AND METHOD OF MANUFACTURE*, assigned to the same assignee and incorporated herein by reference is secured by a suitable medical grade adhesive into one end of the silicone elastomer shell. The self-sealing injection site is then punctured by an inflation device, such as a syringe and needle, to inject a solution of saline or other biologically safe fluid to provide a normal resilient feeling similar to that of the human testicle. Any physiologically safe solution, such as radiopaque contrast media or injectable saline solution may be used to fill the testicular prosthesis.

The manufacturers name and serial number may be laser engraved to the inside of the testicular prosthesis, which is then inked or otherwise marked and covered with a medical grade adhesive to maintain structural integrity of the testicular prosthesis. Alternatively, the characters may be silk screened or other wise appropriately applied to the elastomeric shell interior.

A novel self-presenting suture tab is also incorporated to aid in straight forward suturing where a suture tab is presented having no interfering members which would serve to impede the suture process. The flush but extendable tab is provided at the opposing end of the elastomer shell through which a suture may be attached in order to anchor the prosthesis in the scrotum. It does not normally extend beyond the profile of the prosthesis.

A method for the evacuation of air and excess saline or other physiological solution from the interior of the testicular prosthesis, is provided in which stored energy forces air from an inverted evacuation domed area outwardly through a syringe, which is used to fill the prosthesis initially.

An assembly fixture is provided for alignment of the silicone elastomer shell and the self-sealing injection site prior to adhesive securement of the self-sealing injection site to an opening in an end of the silicone elastomer shell.

According to a preferred embodiment of the present invention, there is provided a testicular prosthesis having a silicone elastomer shell which is filled through a self-sealing fill injection site adhesively secured in one end of the silicone elastomer shell. A non-obtrusive and extendable tab for suture securement is included on the end of the prosthesis opposite the end on which the self-sealing injection site is carried.

A significant aspect and feature of the present invention is the manufacturing method incorporating the fixture for alignment and securement of the self-sealing injection site into the elastomeric shell.

Another significant aspect and feature of the present invention is a serialization and identification method for each individual testicular prosthesis.

Mother significant aspect and feature of the present invention is the use of an inverted evacuation dome in conjunction with stored energy in an inflated testicular prosthesis to expel trapped air and fluid from the prosthesis interior.

A further significant aspect and feature of the present invention is the method of forming an evacuation dome by off-center rotation of an elastomeric shell during adhesive placement.

BRIEF DESCRIPTION OF THE FIGURES

Other objects of the present invention and many attendant advantages thereof be readily appreciated as the same becomes better understood by reference to the following detailed description, when considered in connection with the accompanying drawings, in which like reference numerals designate like parts throughout the Figures thereof and wherein:

FIG. 1 illustrates a perspective view of a testicular prosthesis of the present invention;

FIG. 2 illustrates a cross-sectional view along line 2—2 of FIG. 1;

FIG. 3 illustrates an end view (upper end in FIG. 2) of the testicular prosthesis showing the suture site;

FIG. 4 illustrates a cross-sectional view along line 4—4 of FIG. 2;

FIG. 5 is a perspective view of a preferred injection site of the filament wrapped type as more fully described in the aforementioned co-pending application.

FIG. 6 illustrates a greatly enlarged cross-sectional view along line 5—5 of FIG. 5;

FIG. 7 illustrates an alignment fixture;

FIG. 9 illustrates the elastomeric shell of the prosthesis being rotated off vertical to form an evacuation dome;

FIG. 12 illustrates the serialization and identification area of the testicular prosthesis;

FIG. 13A illustrates a from view of an inverting tool used for inverting or turning a prosthesis inside out;

FIG. 13B illustrates a side view of an inverting tool;

FIG. 14 illustrates the head of the inverting tool of FIGS. 12A and 12B connected to the dimple and suture tab of an empty prosthesis;

FIG. 15 illustrates depressing of the empty prosthesis by the inverting tool;

FIG. 16 illustrates passage of the prosthesis shell wall through its cylindrical bore for inverting the prosthesis;

FIG. 17 illustrates a fully inverted elastomeric prosthesis shell;

DETAILED DESCRIPTION OF THE PREFERRED EMBODIMENTS

Figure 8:
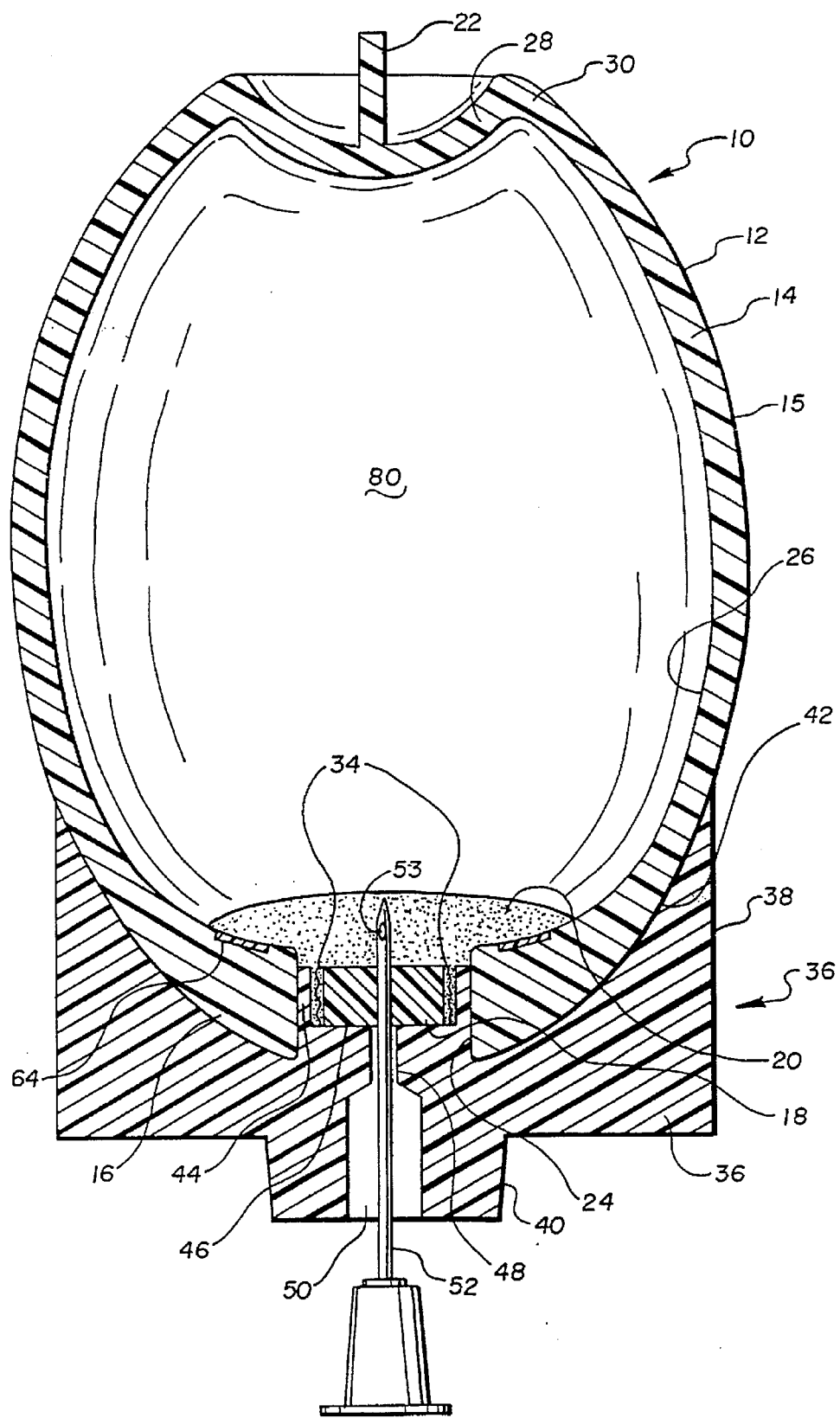
FIG. 8 illustrates the method of injecting adhesive into the interior of the elastomeric shell of the prosthesis when mounting an injection site therein.

FIG. 1 illustrates a perspective view of the testicular prosthesis 10 including a shell 12 which is transfer, injection, compression or otherwise suitably molded from a silicone elastomer such as Dow Corning Q7-4840 or Q7-4735 or an equivalent material, such as NUSIL TECHNOLOGY MED-4735 OR MED 4840. The elastomeric shell 12 is elliptical in longitudinal cross-section to replicate the shape of a testicle and is of a circular shape in transverse cross section. The shell 12 can be produced in a number of sizes to accommodate the proper testicle size required by a patient, and can be filled as required to a preferred firmness or feel. The elastomeric shell wall is approximately 0.030 inches thick on the sides 14 for purposes of example and illustration only, and increasingly tapers to a thickness of 0.170 inches at one end 16 to accommodate a self-sealing injection site 18. Molding with matched cavity and core tooling is the preferred mode of fabrication due to the varying wall thickness of the shell. Dip molding may be used although it is not as precise or as fast. The self-sealing injection site 18 is bonded into an opening 24 in the end 16 of the elastomeric shell 12 by a medical grade adhesive 20 and aligned therein prior to bonding by means of a fixture as described later in detail. A self-presenting suture tab 22 is carried at the opposite end of shell 12 for suturing the shell to the scrotum or other convenient attachment point, if desired.

FIG. 2 illustrates a cross-section of the testicular prosthesis 10 along line 2—2 of FIG. 1. All numerals correspond to those elements previously described. Shell 12 includes an outer surface 15 and an inner surface 26. The thick wall end 16 of elastomeric shell 12 includes the cylindrical bore 24 into which the self-sealing injection site 18, the preferred form of which is the subject of the aforementioned co-pending patent application, is centrally aligned and bonded by a medical grade adhesive 20. Adhesive 20 also bonds to the inner surface 26 of the shell wall 14 over an area thereof as shown in FIG. 12, as well as in the cylindrical bore 24 and to all external sides of the self-sealing injection site 18. An evacuation dome 25 is located above the inner end of self-sealing injection site 18. A dimple 28 at the opposing end 30 of elastomeric shell 12 serves as a shock absorptive mount connecting the relatively thin wall 14 to the suture tab 22 through which a suture may be passed. It is noted that the profile of suture tab 22 conforms generally to the elliptical profile of shell 12 so as not to exceed the device profile. The suture tab 22 may contain a hole 23 which is preferably oval in shape. Alternately, a suture, with or without a needle, may be preattached. A serialization and identification area 64 may also be included on inner surface 26 and is preferably covered by the medical grade adhesive 20, as described later in detail.

FIG. 3 is an end view of end 30 of the testicular prosthesis 10 showing the tab 22 from the top. All numerals correspond to those elements previously described.

FIG. 4 is a cross-sectional view along line 4—4 of FIG. 2. Illustrated in particular is substantially equidistant annular space 54 between self-sealing injection site 18 and cylindrical bore 24 which contains adhesive 20. The self-sealing injection site 18 includes a center elastomeric core 32 bonded by a continuously adhesive coated strand 34 as described in FIG. 5 in more detail. All other numerals correspond to those elements previously described.

FIG. 6 is a cross-sectional view of the self-sealing injection site 18 along line 6—6 of FIG. 5. The injection site shown in FIG. 5 is the type referred to in the aforementioned co-pending application. All numerals correspond to those elements previously described. The center core 32 of self-sealing injection site 18 of these FIGS. 5 and 6 is a silicone elastomer which in fabrication is stretched and then tightly bound while in compression by an adhesive coated fiberglass strand 34 having a plurality of filaments 35a–35n. This procedure holds the center core 32 in compression thereby storing energy in the core and enhancing the self-sealability of the self-sealing injection site 18. This is more fully described in the aforementioned co-pending application. A medical grade flexible adhesive 37, such as silicone adhesive Raumedic Medical Grade Adhesive (SI 1511), adheres strands 34 to themselves and to core 32. Variations in construction of preferred injection site 18 are described in the aforementioned co-pending application.

FIG. 7 illustrates a fixture 36 used for alignment of the self-sealing injection site 18 concentrically with the cylindrical bore 24 of thick end 16 of elastomeric shell 12. All numerals correspond to those elements previously described. Fixture 36 may be made of plastic and includes generally a number of radiused portions including an upper radiused body portion 38 and a lower radiused body portion 40. A cavity 42 conforming to the outer configuration of thick end 16 of elastomeric shell 12 aligns centrally in the upper radiused body portion 38 for subsequent alignment with the same as shown in FIG. 8. Another radiused portion 44 extends upwardly into the region of cavity 42 to closely align within the cylindrical bore 24 of the elastomeric shell thick end 16 as shown in FIG. 8. Three bores 46, 48 and 50 align axially either partially or fully in the radiused portion 44, the upper radiused body portion 38 or the lower radiused portion 40 as illustrated. Bore 46 accommodates self-sealing injection site 18 and bores 48 and 50 accommodate a fill needle 52 as illustrated in FIG. 8.

FIG. 8 demonstrates the method of injecting medical grade adhesive 20 into the interior 80 of elastomeric shell 12 to bond injection site 18 into opening 24. All numerals correspond to those elements previously described. Elastomeric shell 12 is first aligned in the conforming shaped cavity 42 of fixture 36. The radiused portion 44 of fixture 36 aligns centrally within the cylindrical bore 24 of elastomeric shell 12. The self-sealing injection site 18, which is placed in the upper bore 46 prior to alignment of the elastomeric shell 12 with the fixture 36, is also centrally aligned within the cylindrical bore 24. When alignment has been accomplished, a non-coring needle 52 having one or more ports 53 and having a source of thinned medical grade adhesive 20 attached thereto (not shown) is inserted through the bores 50 and 48 and through the self-sealing injection site 18. Adhesive 20 then enters the lower region of the elastomeric shell 12 about and above the vicinity of bore 24 as illustrated such that adhesive 20 covers the lower inner region of elastomeric shell 12, the serialization and identification area 64, and the top inner surface of self-sealing injection site 18. Needle 52 is then withdrawn from injection site 18 and fixture. 36. The elastomeric shell. 12 and fixture 36 are then slowly rotated (shown in FIG. 9) and are progressively tipped from the vertical during rotation to allow adhesive 20 to puddle in an annular fashion around the inner center portion of end 16 to form evacuation dome 25 as illustrated in FIG. 9. The adhesive is then allowed to cure after formation of evacuation dome 25. After curing, fixture 36 is withdrawn from engagement with the elastomeric shell 12 leaving self-sealing injection site 18 concentrically aligned within cylindrical bore 24 and adhered to the lower region of elastomeric shell 12 by the interceding medical grade adhesive 20 as shown in FIG. 10.

FIG. 9 illustrates the elastomeric shell 12 being rotated about an axis 58 which is at a variable angle 60 to the vertical 62. Angle 60 generally is 35°, but can include a range of degrees in that several factors such as but not limited to elastomeric shell 12 size, adhesive viscosity, rate of rotation, angle of rotation, temperature, and adhesive setting time may require different angular settings, different rotation speeds, as well as different rates of tipping, other than described herein. A suitable rotatable clamping device 63 slowly rotates the fixture 36 and the adhesive laden elastomeric shell 12 at a speed of 4 rpm plus or minus one rpm, for example. The viscous adhesive 20 flows outwardly leaving the shaped evacuation dome 25 centered radially about the longitudinal axis of elastomeric shell 12 when shell 12 is tipped at an angle as now described in detail. The axis of rotation 58 is progressively and slowly tipped over a period of about one minute from the vertical axis 62 until reaching the desired angle 60° of 35° which is the most desirable of angles which can range from 35 to 55 degrees depending on the size of elastomeric shell 12 and the other factors previously described. During this slow tipping and rotation, adhesive 20 flows from the area over and about the upper area of self-sealing injection site 18 and along the lower portion of inner surface 26 to remove adhesive 20 from the area overlying self-sealing injection site 18 to form the evacuation dome 25. Alternatively, the elastomeric shell 12 may be spun rapidly from 500 to 1,000 rpm for 10 to 20 seconds, for purpose of example, along the vertical axis to cause the adhesive 20 to flow away from the center to form evacuation dome 25.

Figure 10:
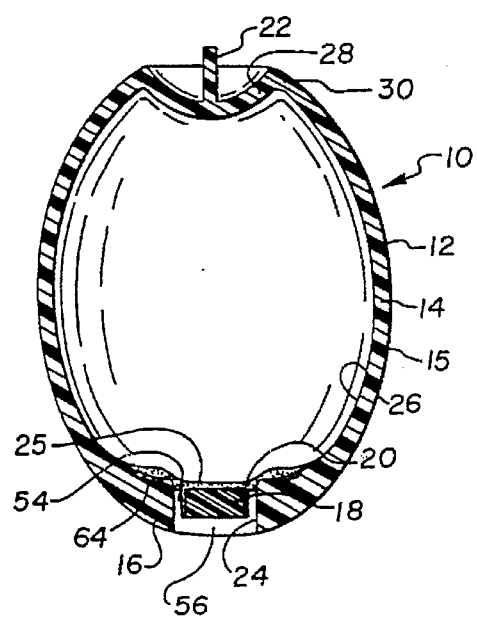
FIG. 10 illustrates the elastomeric shell of the prosthesis and self-sealing injection site subsequent to fixture removal.

FIG. 10 shows the elastomeric shell 12 and the self-sealing injection site 18 subsequent to removal of fixture 36. Again, all numerals correspond to those elements previously described. The self-sealing injection site 18 is suspended concentrically from the adhesive 20 within cylindrical bore 24. An annular space 54 defined by the annular area between the circumferential surface of the self-sealing injection site 18 and the adjacent walls of the cylindrical bore 24 and another circular space area 56 between the plane of the outer surface of the self-sealing injection site 18, the bottom of the annular space 54 and a plane across the outer opening of the cylindrical bore 24 are then back-filled by the medical grade adhesive 20 as illustrated in FIG. 11A to fully and adhesively secure and encapsulate the self-sealing injection site 18 within cylindrical bore 24 of elastomeric shell 12.

Figure 11A:
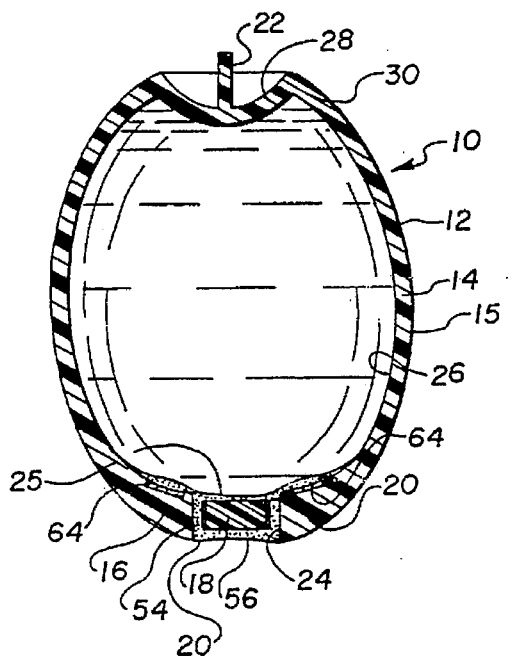
FIG. 11A illustrates complete encapsulation of the self-sealing injection site within the cylindrical bore of the elastomeric shell of the prosthesis.

FIG. 11A illustrates the complete encapsulation of the self-sealing injection site 18 within cylindrical bore 24 of elastomeric shell 12. Again, all numerals correspond to those elements previously described. Backfilling with adhesive 20 of the cylindrical bore 24 in areas 54 and 56 forms a homogenous surroundment of adhesive 20 about the self-sealing injection site 18. The newly applied backfill adhesive, being of the same type, provides for bonding of the previously cured adhesive and the newly applied adhesive to form a homogenous bonding.

Elastomeric shell 12 is of a medical grade low durometer silicone elastomer, thus allowing the elastomeric shell 12 to be soft and resilient. The self-sealing injection site 18 is also preferably constructed of a low durometer medical grade silicone elastomer which has minimal palpability and which is easily compressed. The silicone adhesive 20 when cured and hardened preferably has durometer and elongation qualities similar to the other silicone elastomeric members which it bonds together. The silicone adhesive 20 being medical grade is biocompatable and biostable. Although a compressed self-sealing injection site 18 is incorporated, other suitable valves, such as a diaphragm valve or leaf valve may be used for shell filling. The elastomeric shell may also be dip molded on a mandrel.

Also illustrated in this FIG. 11A is an annular area 64 for serialization and identification of the product. A laser cuts or engraves identification indicia and a serial number within the annular area 64. The laser cuts or engravings are filled with an elastomer containing a dye such as, but not limited to, carbon black to accent the identification indicia and serialization.

The laser engraving, of course, occurs before the medical grade adhesive 20 is applied to the surface 26 for the adhering of the self-sealing injection site 18 within cylindrical bore 24. The accessing of the interior of the elastomeric shell 12 for this purpose is described with reference to FIGS. 13–20. During the process of adhering the self-sealing injection site 18 to the elastomeric shell 12, adhesive 20 flows along and adjacent to the thicker portion 16 and covers, fills in and mends the laser cuts in the annular area 64 to restore and maintain structural integrity, as well as sealing the accenting carbon black or other material from the interior of elastomeric shell 12. The serialization and identification are viewed through the clear elastomeric shell 12 in the area of the thicker portion 16 as depicted in FIG. 12.

Alternatively, the serialization and identification indicia may be silk screened or otherwise suitably adhered or applied to the annular area 64 or any other suitable portion of the inner surface 26.

Figure 11B:
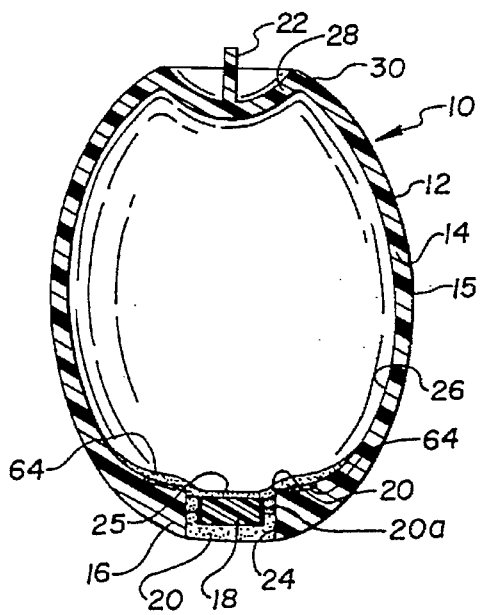
FIG. 11B illustrates radiopaque encapsulation of the self-sealing injection site in a testicular prosthesis.

FIG. 11B illustrates the complete encapsulation of self-sealing injection site 18 and also the incorporation of a band of suitable radiopaque adhesive 20a containing for example barium sulfate ($BaSo_4$) in a range of 14% to provide a radiopaque member surrounding the self-sealing injection site 18 in the upper portion of the annular area of the cylindrical bore 24 surrounding the self-sealing injection site 18. Band 20a is placed in position and then adhesive 20 is backfilled into the remaining area of cylindrical bore 24 about the remaining portion of the self-sealing injection site 18 as before described and in direct adhesion with the barium sulfate laden adhesive 20a. All numerals correspond to those elements previously described.

Figure 11C:
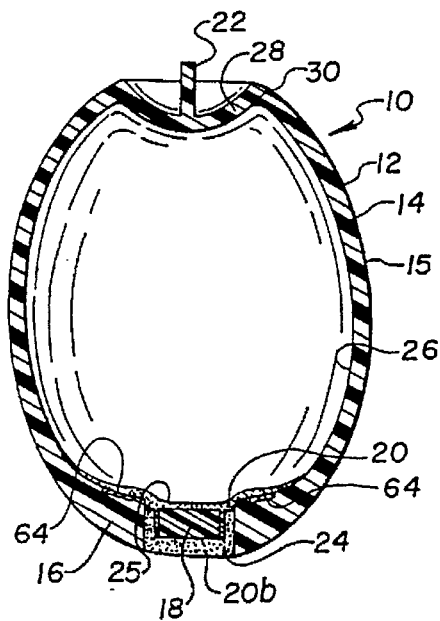
FIG. 11C illustrates radiopaque encapsulation of the self-sealing injection site in a testicular prosthesis.

FIG. 11C illustrates the complete encapsulation of a self-sealing injection site 18 incorporating an alternate band arrangement of suitable radiopaque adhesive 20b containing barium sulfate ($BaSo_4$) in a range of 14% to provide for a radiopaque member surrounding the self-sealing injection site 18. Adhesive 20b is backfilled in areas 54 and 56 of cylindrical bore 24 in direct contact with adhesive 20 to complete the encapsulation of self-sealing injection site 18. All elements correspond to those elements previously described.

FIG. 12 is a top view of the testicular prosthesis 10 showing the serialization and identification area 64 as visible through the thick end 16 of elastomeric shell 12 as previously mentioned. All numerals correspond to those elements previously described.

FIGS. 13A and 13B illustrate a front view and a side view, respectively, of an inverting tool 66 having a handle 68, an essentially rounded head 70 and a groove 72 aligned across and through head 70.

FIG. 14-17 illustrate the method of inverting elastomeric shell 12 (prior to placement of injection site 18) for exposing inner surface 26 and the laser cutting of the serialization and identification area 64 on the interior surface 26 when elastomeric shell 12 has been temporarily turned inside out, thus causing the inner surface 26 to become a temporary "outer surface". All other numerals correspond to those elements previously described. The inverting process starts with the positioning of elastomeric shell 12 to place cylindrical bore 24 in the top most position as shown in FIG. 14. The inside surface 26 is wetted with water and then drained. A small amount of lubricant 74 such as alcohol is then placed in the elastomeric shell through the cylindrical bore 24 and allowed to drain downwardly and around and about the inner surface of the dimple 28.

As illustrated in FIG. 14, head 70 of inverting tool 66 is placed in intimate contact with dimple 28, and the groove 72 of the tool is brought into intimate contact with the suture tab 22. The alcohol or other lubricant 74 facilitates turning the elastomeric shell 12 inside out. Preferably the upper portion of elastomeric shell 12 and the inverting tool 66 are exchanged vertically such that inverting tool 66 is positioned downwardly with respect to elastomeric shell 12 as illustrated in FIG. 15. The inside surface 26 in the vicinity of the lubricant wetted dimple 28 is then pushed through cylindrical bore 24 as illustrated in FIG. 16. FIG. 16 illustrates the engagement and passage of the shell wall 14 through cylindrical bore 24. It is noted that the inner surface 26 at this stage is transitioning from an inner surface to an "outer surface", and the outer surface 15 is transitioning to an "inner surface", all temporarily for the placement of the indicia and the like.

FIG. 17 illustrates the fully inverted elastomeric shell 12 having at this stage been completely reversed to fully transpose interior surface 26 to an "outer surface" and ready the elastomeric shell for laser serialization and identification. The inverting tool is then removed and elastomeric shell 12 rinsed with deionized water and oven dried at 130° F. until dry.

Figure 18:
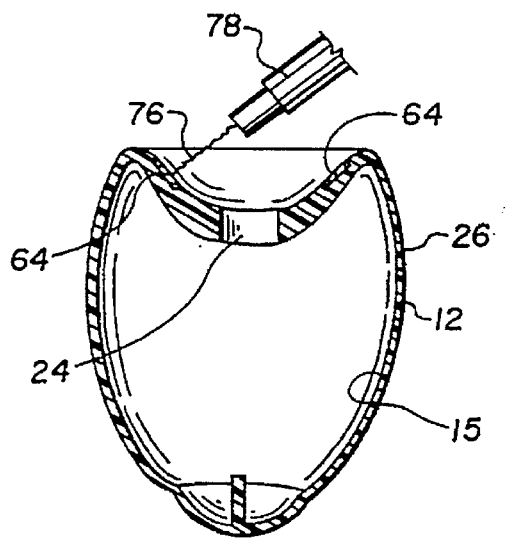
FIG. 18 illustrates the elastomeric prosthesis shell of FIG. 16 reversed for laser engraving with the inserting tool removed.

FIG. 18 illustrates a method of laser cutting the indicia and serialization. All numerals correspond to those elements previously described. Elastomeric shell. 12 having been turned inside out as previously described, thus positioning the former inner surface 26 to the exterior. The annular identification and indicia area 64 is fully exposed so that a laser beam 76 from a laser gun 78 may scribe identification and serialization indicia into the annular area 64. A thin coat of liquid colored silicone elastomer is then applied over the laser engraved areas using a sponge tipped or other suitable applicator. The excess silicone elastomer is removed with a swab and Freon or other suitable solvent. The inked elastomeric shell 12 is then cured at 200° F.±5° F. for a suitable length of time.

Figure 19:
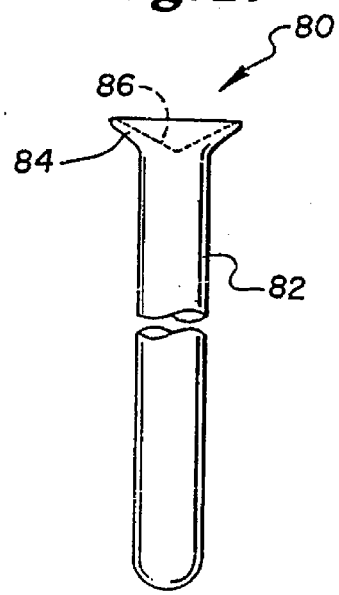
FIG. 19 illustrates a side view of a re-inverting tool for returning the prosthesis to its original condition as shown in FIG. 13.

FIG. 19 illustrates a side view of a re-inverting tool 80 including a handle 82, a truncated cone-like tip 84 and a conical recess 86 in the tip 84.

Figure 20:
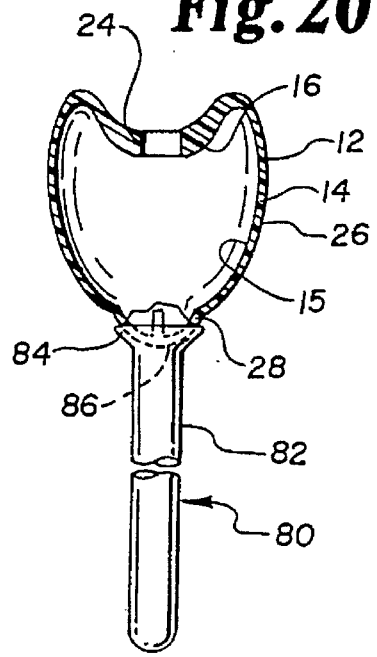
FIG. 20 illustrates engagement of the re-inverting tool with the elastomeric shell of the prosthesis.

FIG. 20 illustrates the engagement of re-inverting tool 80 with the inverted elastomeric shell 12. All numerals correspond to those elements previously described. The re-inverting process is quite similar to the inverting process. Surface 15, now which is presently the "inner surface", is wetted with water and trained. A small amount of lubricant is then introduced for facilitating the re-inverting of elastomeric shell 12. Recess 86 of the re-inverting tool is brought into contact with reversed dimple 28 as shown in FIG. 20. Elastomeric shell 12 and re-inverting tool 80 are vertically reversed to allow the lubricant to flow about surface 15. The reinverting tool is then pushed to extrude the dimple 28 and shell wall 14 through cylindrical bore 24 to completely re-invert the elastomeric shell 12. The re-inverted elastomeric shell is washed and dried and is then ready for further processing as already described above having to do with placement of the injection site and so forth.

Figure 21:
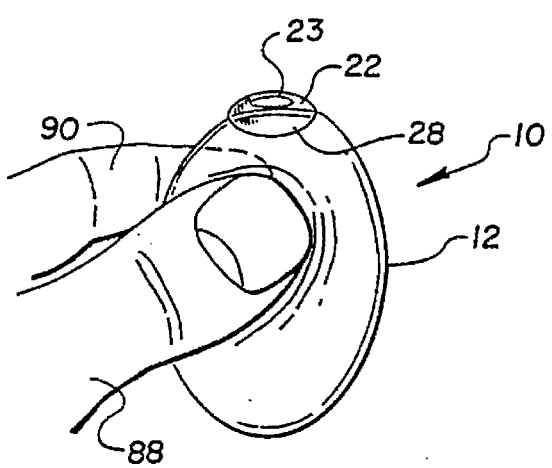
FIG. 21 illustrates the suture tab being presented for suturing by squeezing the prosthesis.

FIG. 21 illustrates the suture tab 22 being presented by grasping and squeezing the upper portion of the testicular prosthesis 10 between a thumb 88 and a finger 90. All other numerals correspond to those elements previously described. This action causes reversal and outward distension of dimple 28 to elevate the suture tab 22 above the elliptical profile curve of elastomeric shell 12, thus presenting a suture tab 22 having unrestricted access. The distension of the suture tab 22 provides clearance for suture needle introduction. This procedure allows suturing with reduced possibilities of puncture of elastomeric shell 12 as suture tab 22 is presented unencumbered by interfering and adjacent surfaces. Flexing of the shell presents the suture tab for, easy suture needle access to reduce puncture vulnerability.

Figure 22:
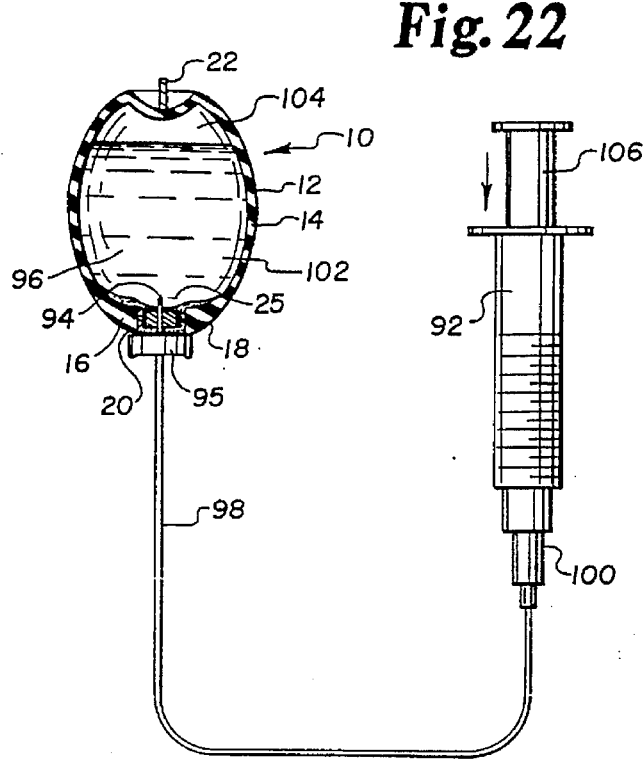
FIG. 22 illustrates the filling of the testicular prosthesis with fluid
Figure 23:
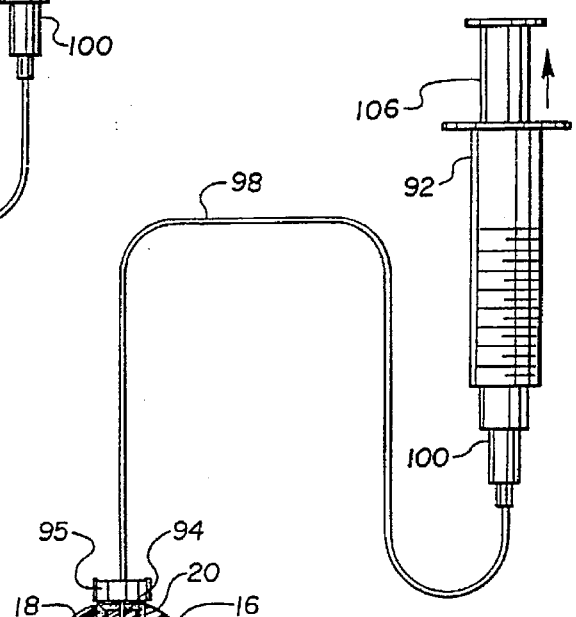
FIG. 23 illustrates the evacuation of air and excess solution from the testicular prosthesis.

FIGS. 22 and 23 illustrate the steps for the preferred method of filling the testicular prosthesis 10 with a saline or other biologically safe fluid. All numerals correspond to those elements previously described. A purged syringe 92 having a non-coring butterfly needle 94 is used to inject and overfill an amount of saline or other suitable solution 96 into the interior of the testicular prosthesis 10 via an infusion line 98, the non-coring butterfly needle 94 and Luer fitting 100. The butterfly needle 94 also includes a planar handle 95 which serves as a stop device to allow penetration of the needle 94 to a predetermined depth as described later in detail. The non-coring butterfly needle 94 is inserted through the medical grade adhesive 20, through the self-sealing injection site 18 and just beyond the evacuation dome 25 into the interior 102. Preferably prosthesis 10 is maintained upright as shown in the Figure during filling but this is not necessary. The syringe plunger is slowly depressed to distend (indicated by the arrows) the testicular prosthesis 10 to about 1 to 1½ times its empty size. Solution 96 forcibly enters the interior 102 and causes several actions. Firstly, air 104 in the elastomeric shell 12 is compressed by the incoming solution 96. Secondly, the wall 14 of the elastomeric wall is expanded outwardly due to the action of the incoming solution 96 and the compression of the air 104. Stored energy caused by these actions is later used to evacuate the air 104 from the interior 102 as described with reference to FIG. 23. More solution 96 is injected into the interior 102 than is normally required. Any excess solution can be drained off during the evacuation process to give the right "feel" to the testicular prosthesis 10. It is important to note that the butterfly needle 94 is of a non-coring type where the ports are included in the side wall of the needle to avoid any material being cored out or loosened by a needle. Cores could cause possible clogging during the air evacuation process as now described with reference to FIG. 23.

FIG. 23 illustrates the air evacuation portion of the filling method. All numerals correspond to those elements previously described. The filled testicular prosthesis 10 is inverted causing the contained air 104 to migrate from near the suture end to the end nearest the evacuation dome 25, which is adjacent to the now upwardly positioned self-sealing injection site 18. The testicular prosthesis 10 is gently shaken until all internal air 104 is one large bubble in the upper end. Once this is accomplished, the plunger 106 of syringe 92 is progressively withdrawn. The stored energy in the testicular prosthesis 10 causes the compressed air 104 to exit through the port(s) of the butterfly needle 94 as the plunger 106 is manually released and the air travels to the top of syringe 92. Walls 14 which were outwardly and forcibly expanded during the first portion of the filling process, now relax inwardly (indicated by arrows) to assist in expelling of any remaining air 104. As this occurs, the level of solution 96 approaches evacuation dome 25. Air 104 is concentrated at this point in the procedure substantially to the area of the evacuation dome 25 where the air and any desired amount of excess solution 96 is subsequently drawn off through butterfly needle 94. When air 104 is expelled and when the desired inflation by solution 96 of the testicular prosthesis 10 is reached, butterfly needle 94 is withdrawn and the self-sealing injection site 18 seals the puncture caused by the butterfly needle 94, thus sealing the interior 102 of the testicular prosthesis 10. The self-sealing injection site 18 can be punctured repeatedly permitting adjustment of the fluid volume if desired.

Figure 24:
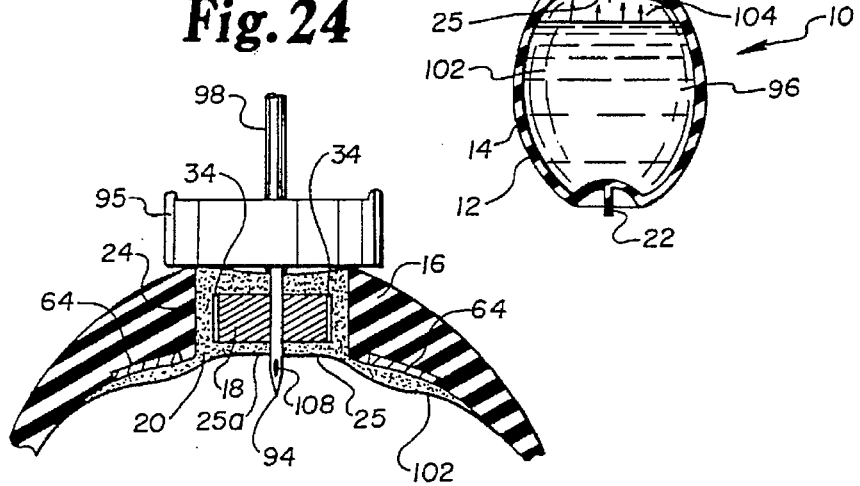
FIG. 24 illustrates a butterfly needle penetrating the evacuation dome of the testicular prosthesis.

FIG. 24 shows the butterfly needle 94 penetrating the evacuation dome 25. All numerals correspond to those elements previously described. Handle or collar 95 acts as a stop and is located at a predetermined point along needle 94 allowing the orifice(s) 108 to be precisely located at the same level and coinciding with the upper most portion of the evacuation dome 25. The preferred placement of the orifice(s) 108 is as illustrated, where the orifice(s) 108 straddle the evacuation dome area 25a, which is the upper most central area of the evacuation dome 25 when the testicular prosthesis 10 is positioned for removal of air 104 and some of solution 96. This coinciding orifice-to-dome relationship insures withdrawal of some solution, and more importantly, of air 104 from the uppermost portion of the interior 102. The use of the handle or collar 95 as a stop prevents the butterfly needle 94 from extending too far into the interior 102 which would allow only removal of air 104 or solution 96 up to the level of the orifice(s) 108. This could be lower than that of the evacuation dome surface 25a if not properly placed. The use of handle or collar 95 also insures that butterfly needle 94 will not be inserted to an insufficient depth whereby the orifice(s) 108 are buried in the residing self-sealing injection site 18, thus restricting outward flow from the interior 102 of the testicular prosthesis 10.

Various modifications may be made to the present invention without departing from the apparent scope of the following claims.

While this invention may be embodied in many different forms, there are described in detail herein specific preferred embodiments of the invention. This description is an exemplification of the principles of the invention and is not intended to limit the invention to the particular embodiments illustrated.

The filling method has been described as being accomplished preoperatively i.e., immediately before implantation or at the time of manufacture as a prefill. However, it may be readily accomplished postoperatively i.e., after implantation as well.

What is claimed is as follows:

1. A method for filling a prosthesis having an elastomeric shell and a self-sealing injection site with a fluid using an injection needle having at least one opening, said elastomeric shell defining an interior, said method comprising the steps of:

inserting the injection needle through the self-sealing injection site;

injecting a sufficient quantity of the fluid through the injection needle and the self-sealing injection site to provide excess fluid within the interior of the elastomeric shell so as to expand the elastomeric shell and compress air disposed within the interior;

orienting the prosthesis such that the self-sealing injection site is disposed so as to allow air within the interior of the elastomeric shell to collect in the proximity of the self-sealing injection site; and withdrawing the air from within the interior of the elastomeric shell through injection needle having the opening aligned proximate to the injection site.

2. The method of claim 1 wherein the fluid in the interior of the elastomeric shell defines a volume, and wherein the method further comprises the step of:

adjusting the volume of the fluid within the interior of the elastomeric shell to obtain a desired palpability of the elastomeric shell.

3. The method of claim 1 wherein the fluid is a physiological saline solution.

4. The method of claim 1 wherein the prosthesis is an artificial testicle.

5. The method of claim 1 wherein the prosthesis is implanted within a patient, and the steps of injecting the fluid into the interior of the elastomeric shell and withdrawing the air from within the interior of the elastomeric shell are performed preoperatively immediately prior to implantation of the prosthesis within said patient.

6. The method of claim 1 wherein the prosthesis is implanted within a patient, and the steps of injecting the fluid into the interior of the elastomeric shell and withdrawing the air from within the interior of the elastomeric shell are performed subsequent to implantation of the prosthesis within the patient.

7. The method of claim 1 wherein the elastomeric shell is fabricated and the self-sealing injection site is attached to the elastomeric shell, and further wherein the steps of injecting the fluid into the interior of the elastomeric shell and withdrawing the air from within the interior of the elastomeric shell are performed substantially contemporaneous with fabricating the elastomeric shell and attaching the self-sealing injection site.

8. The method of claim 1 wherein the injection needle includes a collar for controlling the extent of the length of the injection needle inserted into the interior of the elastomeric shell.

9. The method of claim 8 wherein the injection needle has an end, and the collar is positioned a predetermined distance from said end of the injection needle to align the opening of the injection needle generally proximate to the injection site when the injection needle is inserted into the interior of the elastomeric shell.

10. The method of claim 1 wherein the elastomeric shell is oriented in a first position for inserting the fluid and is reorientated to a second position for withdrawing the air from the interior of the shell.

11. A method for filling an interior of a flexible, inflatable shell of a prosthesis with a fluid using an injection device having at least one opening, said method comprising the steps up:

inserting the injection device through an injection site into the interior of the flexible, inflatable shell for filling the interior with the fluid;

injecting the fluid into the interior of the shell;

orienting the prosthesis such that air accumulates at a selected region of the interior of the shell;

positioning the opening of the injection device relative to the selected region of the interior of the shell where air has accumulated such that the opening of the injection device is disposed within the selected region; and withdrawing the air through the opening of the injection device to purge the air from the interior of the flexible, inflatable shell of the prosthesis.

12. The method of claim 11 wherein the flexible, inflatable shell is formed of an elastomeric material.

13. The method of claim 12 wherein the interior of the flexible, inflatable shell is filled with an excess amount of the fluid to expand the flexible, inflatable shell and compress the air disposed within the interior of the flexible, inflatable shell.

14. The method of claim 13 further comprising the step of:

draining the excess fluid from the interior of the flexible, inflatable shell.

15. The method of claim 11 further including the step of:

shaking the flexible, inflatable shell to force the air to the selected region of the interior of the flexible, inflatable shell.

16. The method of claim 11 wherein the flexible, inflatable shell of the prosthesis is oriented such that the air disposed within the interior of the shell accumulates proximate to the injection site and the injection opening of the injection device is generally aligned relative to the injection site for withdrawing the air.

17. The method of claim 11 wherein the injection site is a self-sealing injection site.

18. The method of claim 11 wherein the flexible, inflatable shell is orientated in a first position for inserting the fluid and is reorientated to a second position for withdrawing the air from the interior of a shell.

* * * * *